(12) United States Patent
Koka et al.

(10) Patent No.: US 6,916,496 B2
(45) Date of Patent: Jul. 12, 2005

(54) PROCESS FOR MANUFACTURING CHEESES AND OTHER DAIRY PRODUCTS AND PRODUCTS THEREOF

(75) Inventors: Ramarathna Koka, Mt. Prospect, IL (US); David W. Mehnert, Antioch, IL (US); Rudolf J. Fritsch, Chicago, IL (US); Wolfram Steffan, Ottobrunn (DE); Peter Habermeier, Scheyern (DE); Allan G. W. Bradbury, Rohrmoos (DE); Alan Wolfschoon-Pombo, Freising (DE); Mehran Rose, Hohenbrunn (DE)

(73) Assignee: Kraft Foods R&D, Inc., Munich (DE)

( * ) Notice: Subject to any disclaimer, the term of this patent is extended or adjusted under 35 U.S.C. 154(b) by 44 days.

(21) Appl. No.: 10/702,718

(22) Filed: Nov. 6, 2003

(65) Prior Publication Data

US 2004/0151802 A1 Aug. 5, 2004

Related U.S. Application Data

(63) Continuation of application No. PCT/US02/14337, filed on May 7, 2002.
(51) Int. Cl.[7] ............................. A23C 9/00; A23C 19/00
(52) U.S. Cl. ........................... 426/39; 426/36; 426/582; 426/583
(58) Field of Search ............................. 426/34, 36, 39, 426/40, 580, 582, 583

(56) References Cited

U.S. PATENT DOCUMENTS

| 2,746,916 A | | 5/1956 | Magariello | |
|---|---|---|---|---|
| 5,405,641 A | * | 4/1995 | Kurihara et al. | 426/655 |
| 5,851,578 A | * | 12/1998 | Gandhi | 426/590 |

FOREIGN PATENT DOCUMENTS

GB        1 325 727        8/1973

* cited by examiner

*Primary Examiner*—Leslie Wong
(74) *Attorney, Agent, or Firm*—Fitch, Even, Tabin & Flannery

(57) ABSTRACT

Process for manufacturing cheeses and other dairy products, and the resulting products, in which lactobionic acid is added, or generated in situ, in combination with a dairy component in the course of the process. The lactobionic acid can be used as the sole acidulent for direct acidification of the cheese, or in conjunction with reduced amounts of lactic acid culture. When the lactobionic acid is generated in situ during cheese manufacture according to the invention, a lactose oxidase is used in one embodiment to convert lactose intrinsically present in the dairy liquid ingredient(s) into lactobionic acid. The organoleptic attributes of the cheeses made using lactobionic acid as an ingredient are satisfactory and fully suitable. The process can be applied to the production of a wide variety of cheeses, including, for example, cream cheeses, hard cheeses such as cheddar, UF cheeses, process cheeses, cheddar cheeses, and so forth.

37 Claims, 8 Drawing Sheets

PROCESS FOR MANUFACTURING CHEESES AND OTHER DAIRY PRODUCTS AND PRODUCTS THEREOF

RELATED APPLICATION

This is a continuation of prior application No. PCT/US02/14337 and designating the U.S., filed May 7, 2002, which is hereby incorporated herein by reference in its entirety.

This application is based on, and claims benefit of, European Patent Application No. 01110166.4, filed on May 7, 2001, and which is hereby incorporated by reference.

FIELD OF THE INVENTION

The present invention generally relates to a process for manufacturing cheese products and other dairy products, and more particularly, to a process for manufacturing cheese products and other dairy products using lactobionic acid and to the resulting products thereof.

BACKGROUND OF THE INVENTION

Cheeses are generally made by adding a microorganism to milk which is capable of metabolizing lactose to produce lactic acid and develop acidity. The milk is usually set with a milk clotting or coagulation enzyme, such as rennet, or by developing acidity to the isoelectric point of the casein. Enzyme coagulation of milk also requires an acidic environment. The milk is inoculated with a bacterial culture or starter culture which produces sufficient lactic acid for the rennet to work. The coagulum or curd that results generally incorporates transformed casein, fats including natural butter fat, and flavorings that arise (especially when a bacterial culture is used). The coagulated milk is cut, whey separated and then recovered from the resulting curd. The curd may be pressed to provide a cheese block; curing may take place over a period of time under controlled conditions. For instance, a hard cheese such as cheddar cheese may be cured from about 10 days to one year or more, depending on the desired cheese flavor and body breakdown.

It also is well known to provide a cheese product having some of the characteristics of natural cheese by comminuting one or more natural cheeses, and heating the cheese with an emulsifying agent. The name given to the resulting product depends upon the ingredients used and its composition and, in some instances, is determined by Regulations promulgated by the U.S. Food and Drug Administration, known as Standards of Identity. For example, the term "pasteurized process cheese" refers to a product comprising a blend of cheeses to which an emulsifying agent, and possibly acids, are added, and the mixture is then worked and heated into a homogeneous, plastic mass. Under the current Standards of Identity, the moisture level of process cheese generally does not exceed about 44 percent and process cheese has a minimum fat level of about 40 percent on a dry basis.

It is also known that natural cheese can be manufactured using concentrated milk which has been prepared by membrane processing, such as ultrafiltration, in which milk is cycled across a semi-permeable membrane at an elevated pressure such that water and low molecular weight components pass through the membrane, while certain proteins and fats are retained by the membrane. Cheese making cultures are added to the obtained concentrated milk which is then fermented, usually in the presence of a milk coagulating enzyme, such as rennet, to provide a coagulum. The resulting coagulum is cut or broken to cause syneresis resulting in whey separation. The whey is drained and the curd is processed. The type of cheese cultures used and the processing varies with the desired cheese product. The curd may then be salted, placed in molds, and pressed to allow further whey drainage. The cheese is then ripened to the extent desired.

Cream cheese is an acid-coagulated, non-cured cheese made of dairy components including cream. Cream cheese, which is normally stored under refrigeration conditions, has a smooth and butter-like consistency with a delicate dairy flavor profile, which does not accommodate off-flavors. The texture and body of cream cheese at refrigeration temperatures is generally such that the cream cheese can be sliced and spread. In making cream cheese, sweet cream and dry milk-derived solids or milk are typically blended with a dry blend of vegetable gum and salt in preselected proportions to form a cream cheese mix. The cream cheese mix normally has a butterfat content of from about 10 to about 14 percent (and in certain make procedures up to as much as 20 percent), so that after processing, the finished cream cheese product will have a butterfat content of at least about 33 percent of the product, and a total milk solids content of at least 45 percent corresponding to the presence of not more than about 55 percent moisture in the cream cheese product.

The cream cheese mix is inoculated with a lactic acid culture. Rennet may be used to aid the coagulation of the mix. The mix is cultured by holding it at the inoculation temperature until it has ripened and a coagulum is formed. The acidity of the coagulum may typically be in the range of from about 0.6 to about 0.9 percent (calculated as percent equivalent lactic acid), and the pH of the cultured coagulum may typically be in the range of from about 4.2 to about 5. The resulting coagulum is exposed to a temperature of about 180° F. for a brief period of time and then centrifuged to separate the curd from the whey, and then the cream cheese product is cooled and packaged. Cream cheese generally contains about 2 to about 3 percent lactose.

Lactose (4-O-β-D-galactopyranosyl-D-glucopyranose), commonly called milk sugar, is the primary carbohydrate of milk. Lactose is a low value sugar in food systems because of lactose intolerance and due to its contribution to browning reactions and crystallization. The use of milk substitutes or reduced dairy content in cheese mixes to reduce lactose content in the produced cheese may not provide acceptable products from standpoints of complying with Standards of Identity regulations, processability, and/or ultimate product physical properties and flavor characteristics.

Lactobionic acid (4-O-β-D-galactopyranosyl-D-gluconic acid; CAS Reg. No. 96-82-2) is a water soluble, white crystalline compound and can be synthesized from lactose by oxidation of the free aldehyde group in lactose as carried out catalytically, chemically, electrolytically, or enzymatically. Harju, *Bulletin of the IDF* 289, ch. 6., pp. 27–30, 1993; Satory et al., *Biotechnology Letters* 19 (12) 1205–08; 1997. The use of lactobionic acid or its salts as additives in food products previously has been suggested for several specific applications. Calcium or iron chelate forms of lactobionic acid has been described for dietary mineral supplementation. Riviera et al., *Amer. J. Clin. Nutr.;* 36 (6) 1162–69, 1982. U.S. Pat. No. 5,851,578 describes a clear beverage having a non-gel forming fiber, and water soluble salts of calcium, with or without water soluble vitamins, with or without additional mineral salt supplements and buffered with food acids. The food acid buffering agent includes citric, lactic, maleic, adipic, succinic, acetic, acetic gluconic, lactobionic, ascorbic, pyruvic, and phosphoric acids, as well as combinations thereof. Calcium lactobionate, a salt form of lactobionic acid, has been approved for use as a firming agent in dry pudding mixes. 21 C.F.R. §172.720 (1999). Also, the possible use of lactobionic acid as a general food acidulent has been proposed, albeit without exploration or illustration. Timmermans, *Whey: Proceedings of the 2nd Int'l Whey Conf.,* Int'l Dairy Federation, Chicago, October 1997, pp. 233, 249. This article generally describes lactobionic acid as being useful as an antibiotics carrier, an organ transplant preservative, mineral supplementation, growth promotion of bifidobacteria, or as a co-builder in detergents in its K-lactobionate salt form.

It would be desirable to manufacture cheeses with reduced lactose content while preserving flavor, texture, and appearance characteristics comparable with conventional cheese products. It would also be desirable to reduce starter culturing requirements and the time associated therewith in cheese production, while maintaining acceptable organoleptic attributes. It would also be desirable to increase the solids levels in manufactured cheeses while using reduced amounts of starter cultures as compared to conventional practice. It would also be desirable to be able to use higher lactose containing whey concentrates in cream cheese formulations without the need to increase the usage of cultures. The present invention provides. such methods and products in which lactobionic acid is provided in a cheese mix.

SUMMARY OF THE INVENTION

The present invention relates to a process for manufacturing cheeses and other dairy products, and the resulting products, in which lactobionic acid is added, or generated in situ, in combination with a dairy component in the course of the process. The cheeses and other dairy products made according to this invention have fully acceptable organoleptic attributes, while permitting reductions in processing time, and/or the requirements for other ingredients, such as starting cultures and/or rennet. Process flexibility is provided in this way, as well as increased production yields and possible savings in ingredient costs. For purposes of this invention, the term "lactobionic acid" is intended to include lactobionic acid as well as edible salts thereof (e.g., alkali and alkaline earth salts, ammonium salts, and the like).

It has surprisingly been found that lactobionic acid can be used for direct acidic coagulation of cheeses, such as cream cheeses, without the need to use culturing and/or rennet. Lactobionic acid also has a pH-decreasing effect on cheese mixes, such that it acidifies dairy components used in cheese production, such as milk, sweet creams, and whey. In addition, lactobionic acid has a sweet acidic taste that has been found to be compatible with cheese products. The resulting cheese products made with lactobionic acid have fully acceptable flavor, appearance, texture, and mouthfeel attributes.

In another embodiment, lactobionic acid is used to reduce, and optionally even eliminate, the amount of cheese starting culture used in cheese manufacture, such as hard cheese or ultrafiltered (UF) cheese production. A starting culture, as referenced in this context, generally means a lactic acid bacteria. In the instance of hard cheese production, such as cheddar cheese production, the lactobionic acid introduced to the cheese mix is used to partially replace and reduce the amount of starting cultures that otherwise normally would be used, which effectively aids the acidification of the cheese mix. This procedure provides a cheese product including a mixture of lactic acid and lactobionic acid, which improves yield. The lactobionic acid also can be used as an ingredient in process cheese production, yielding acceptable products.

The lactobionic acid can be added to a cheese mixture in a process according to any of the embodiments described herein to provide these effects in its free acid form, or as a consumable salt form thereof, or in a pH neutralized form. Neutralized form, for purposes herein, means that lactobionic acid is neutralized, prior to admixture with the cheese mix, in an aqueous solution to a pH of about 7 by admixture therewith an alkaline agent that will yield biocompatible neutralization products, such as an alkali metal hydroxide like sodium hydroxide or potassium hydroxide, or an alkaline earth metal hydroxide such as calcium hydroxide, or an alkaline earth metal carbonate such as calcium carbonate.

In another advantageous mode of the invention, which is applicable to all the various cheese-making and other dairy product-making embodiments described herein that employ one or more lactose-containing dairy component ingredients in the cheese mix, the lactobionic acid can be introduced to the cheese mixture through its in situ generation by catalytic action of an added carbohydrate oxidase enzyme on the lactose present in the dairy component(s) of the cheese mixture. Suitable carbohydrate oxidase enzymes include, for example, lactose oxidase, glucose oxidase, hexose oxidase, and the like, as well as mixtures thereof. Generally, lactose oxidase is preferred.

The in situ generation of lactobionic acid in a cheese mix during cheese manufacture gives rise to a multitude of beneficial effects. First, it effectively reduces the lactose content of the original dairy component(s) of the cheese mixtures, permitting lactose-reduced products to be achieved. Therefore, among other things, this aspect of the invention can be used for the production of lactose-reduced cheese products. Alternatively, it allows the use of relatively richer-lactose ingredients in the original cheese mix, due to the conversion of a portion of the lactose content thereof to lactobionic acid, as will occur during the course of cheese making after the lactobionic acid is generated. In addition, lactobionic acid has a mass weight that is approximately four times greater than that of lactic acid. Consequently, the lactobionic acid retained in the cheese product, which has been derived from the catalytic conversion of lactose, has a much greater mass, on an equi-molar basis, than the lactose converted to lactic acid. This effect enhances the appearance, texture and mouthfeel of the cheese product. In this way, the lactobionic acid can act as a bulking agent. For purposes herein, the term "bulking agent" means an agent which mimics the effects of natural fat and/or protein in cheese compositions insofar as its effects on the appearance (e.g., firmness, opacity) and textural qualities (e.g., lubricity, smoothness, mouthfeel) of the cheese.

In general, the proportion of lactobionic acid added to a cheese mix, or generated in situ via enzymatic lactose conversion as catalyzed by carbohydrate oxidase addition, to provide one or more of these advantageous effects, ranges from about 0.1 to about 10 percent, particularly from about 2 to about 6 percent, and more particularly from about 3 to about 5 percent, based on the total weight of the cheese mix before separation of curd and whey.

The whey products of cheeses made using lactobionic acid according to this invention, and which therefore retain a portion of the lactobionic acid ingredient, also can be recycled, instead of being completely discarded as waste, for use as starting ingredients in separate cheese production batches or runs used for making process cheeses or cream cheeses. Alternatively, the whey product of a natural cheese making procedure can have the lactobionic acid or lactose oxidase added thereto, and the so-treated whey product can be used as a starting ingredient in the separate manufacture of process cheeses, cream cheeses, or other dairy products (including, for example, whey beverages, whey-containing power or candy bars, and the like).

The invention is remarkable in its versatility. Experimental studies, as described herein, demonstrate its applicability in the manufacture of widely varied types of cheeses including cream cheeses, hard cheeses, and pasteurized process cheeses. The invention also has been successfully demonstrated in the manufacture of so-called UF cheeses made from ultrafiltered (UF) concentrated milk. The invention also has been successfully demonstrated in the manufacture of other dairy products such as, for example, sour cream, yogurt, milk, reduced-lactose milk, and the like. Cheeses and other dairy products prepared with and/or containing lactobionic acid according to this invention have acceptable tastes and textures similar to the conventional cheeses and other dairy products of the corresponding kind.

The cheese products containing lactobionic acid also have improved product stability due to the preservative effect of the lactobionic acid. As an added advantage, the chelation properties of the lactobionic acid can be utilized as a milk-derived delivery vehicle in calcium supplementation of food products.

BRIEF DESCRIPTION OF THE DRAWINGS

Other features and advantages of the present invention will become apparent from the following detailed description of preferred embodiments of the invention with reference to the drawings, in which.

DETAILED DESCRIPTION OF THE INVENTION

Figure 1:
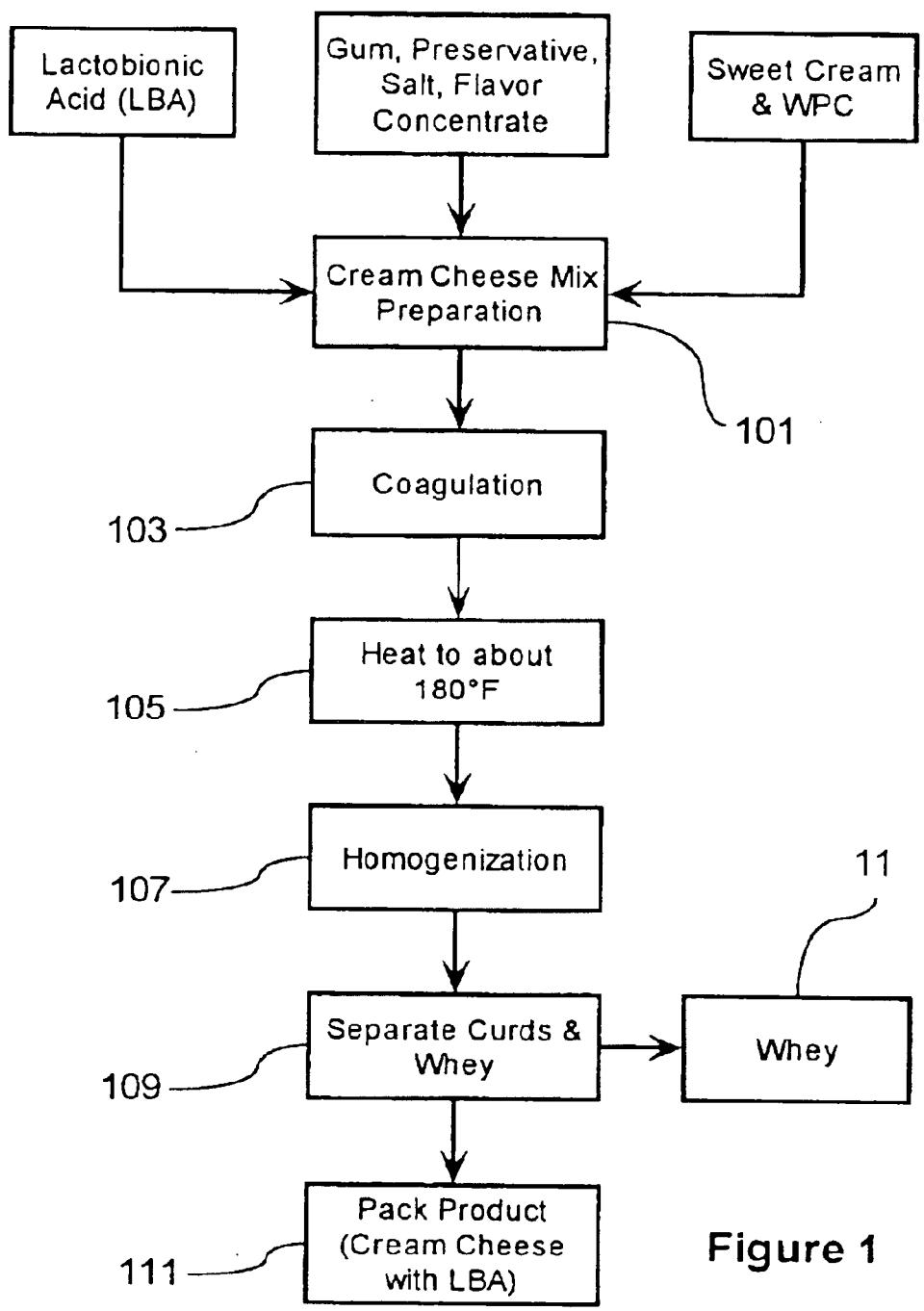
FIG. 1 is a flow chart of steps used in an embodiment of the invention for production of cream cheese.

Referring to FIG. 1, a general process scheme according to one embodiment of the invention is illustrated in which lactobionic acid is used for direct acidic coagulation of a cream cheese, without culturing or the addition of rennet. The cream cheese made is a soft, mild, acid-coagulated non-cured cheese made of dairy products including cream, such as mixtures of cream and whey protein concentrate. As indicated in step 101, the consistency of the cream cheese composition, permitting spreadability while retaining firmness, is modulated by the addition of a vegetable gum, such as bean carob gum. Salt and a preservative is added. Any lack of cultured notes in the directly acidified cheese can optionally be overcome by using flavoring systems for creating the desired cheese flavor. The dairy fluid and whey protein concentrate are added in suitable proportions to provide a cheese mix that can be processed according to the invention to provide a cream cheese having a milk fat content of least about 33 percent, and a moisture content not exceeding about 55 percent based on the weight of the cream cheese product.

The lactobionic acid is added in an amount effective to reduce the pH to the isoelectric point (i.e., about 4.52) of the casein in the dairy ingredients. The proportion of lactobionic acid added to the cream cheese mix generally ranges from about 0.1 to about 10 percent, particularly from about 2 to about 6 percent, and more particularly from about 3 to about 5 percent, based on the total weight of the cheese mix before separation of curd and whey.

The lactobionic acid can be added to the cheese mix directly as an extraneous ingredient in its free acid form, or, alternatively in salt form or in neutralized acid form. The free acid form reduces the pH of the cheese blend. The cheese mix formulation can be adjusted to compensate for any reductions in pH that are greater than desired for optimal coagulation and physical properties in the product. The neutralized form of the lactobionic acid does not impact the pH of the product. In salt form, the lactobionic acid generally is provided as an alkali salt or an alkaline earth metal salt, such as a sodium salt, a potassium salt, or a calcium salt thereof; of course, other lactobionic salts can be used, if desired, so long as they are acceptable for use in food products. The neutralized form of the lactobionic acid can be prepared by neutralizing lactobionic acid dissolved in an aqueous solution, such by addition thereto of an alkaline agent such as sodium or potassium hydroxide sufficient to adjust the pH of the solution to about 7.

As shown in FIG. 1, a cheese mix is thoroughly blended and coagulates due to the acidity of the lactobionic acid (step 103), or other acid added in the case of using neutralized lactobionic acid. The mix is then heated to about 180° F. for about 5 minutes for a short-time pasteurization treatment (step 105), and thereafter is homogenized (step 107). In step 109, the curds and whey can be separated by any conventional technique, including, for example, centrifugation, filtration, mechanical treatment, and the like. The curd product can be packaged cold or hot, and thereafter is stored cold. The cream cheese product (111) and the whey (113) contain lactobionic acid. The whey product containing the lactobionic acid can be reused as a starting ingredient in subsequent cream cheese mixes. This reduces the amount of waste and makes the processing operation more efficient. The introduction of lactobionic acid (whether free, salt form or neutralized) does not bring about any undesirable organoleptic attributes, such as off flavors, in the cream cheese product, while the texture, appearance and mouthfeel is comparable with conventionally manufactured cream cheese.

Figure 2:
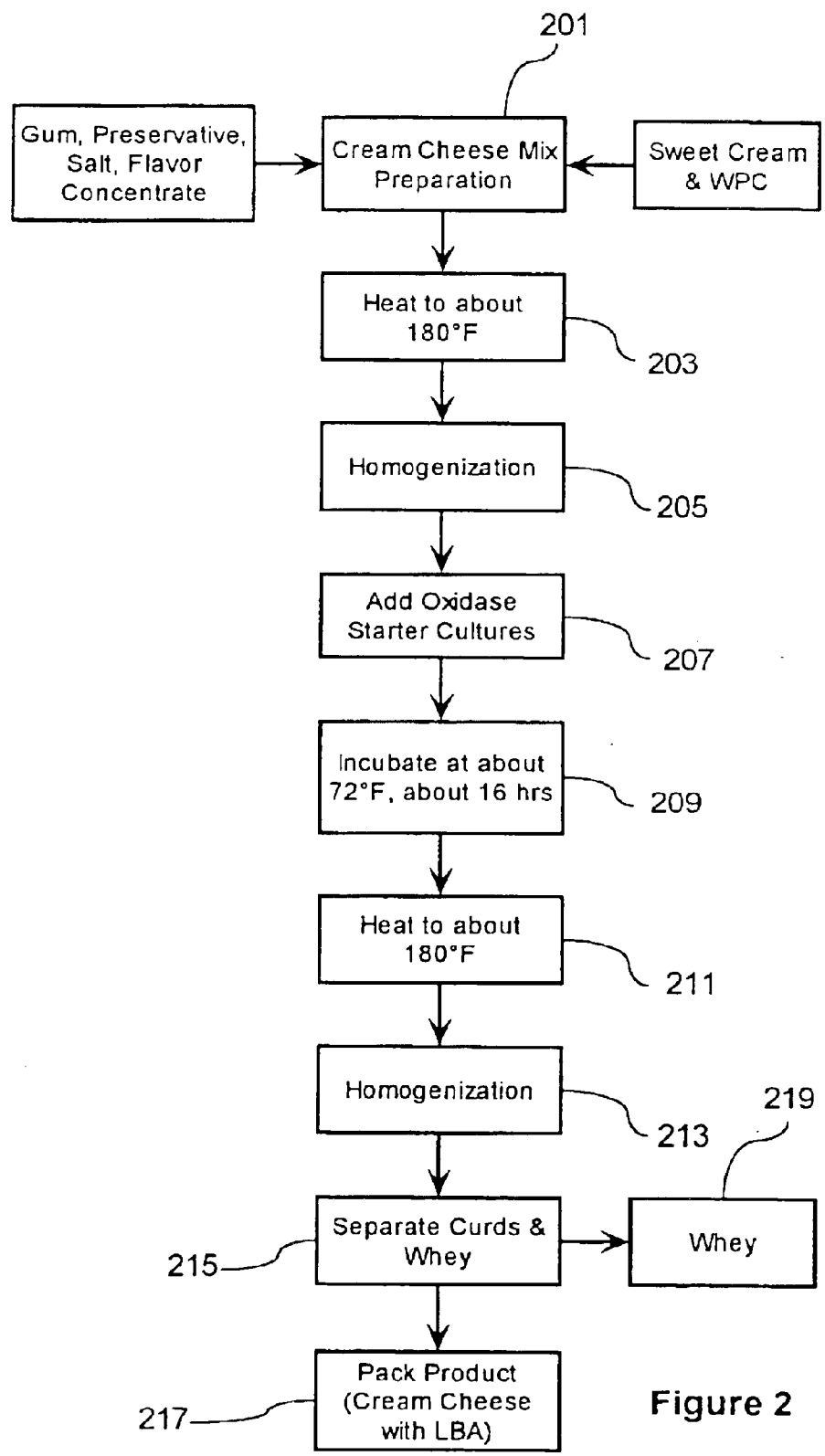
FIG. 2 is a flow chart of steps used in another embodiment of the invention for production of cream cheese.

Referring now to FIG. 2, cream cheese is prepared according to another aspect of the invention in which lactobionic acid is generated in situ in the cream cheese mix via lactose conversion as catalyzed by lactose oxidase addition. In this process scheme, the cream cheese mix is prepared (step 201), and then it is pasteurized (step 203) and thereafter homogenized (step 205). At this juncture (step 207), an oxidase enzyme is added which catalyzes the in situ oxidization of lactose present in the dairy liquids to lactobionic acid. The lactobionic acid generated has a pH-reducing effect on the cheese mix. Suitable oxidases in this respect include, for example, lactose oxidase, cellobiose dehydrogenase, glucose-fructose oxidoreductase, hexose oxidase, and any other oxidases having the above-mentioned functionality.

Figure 7:
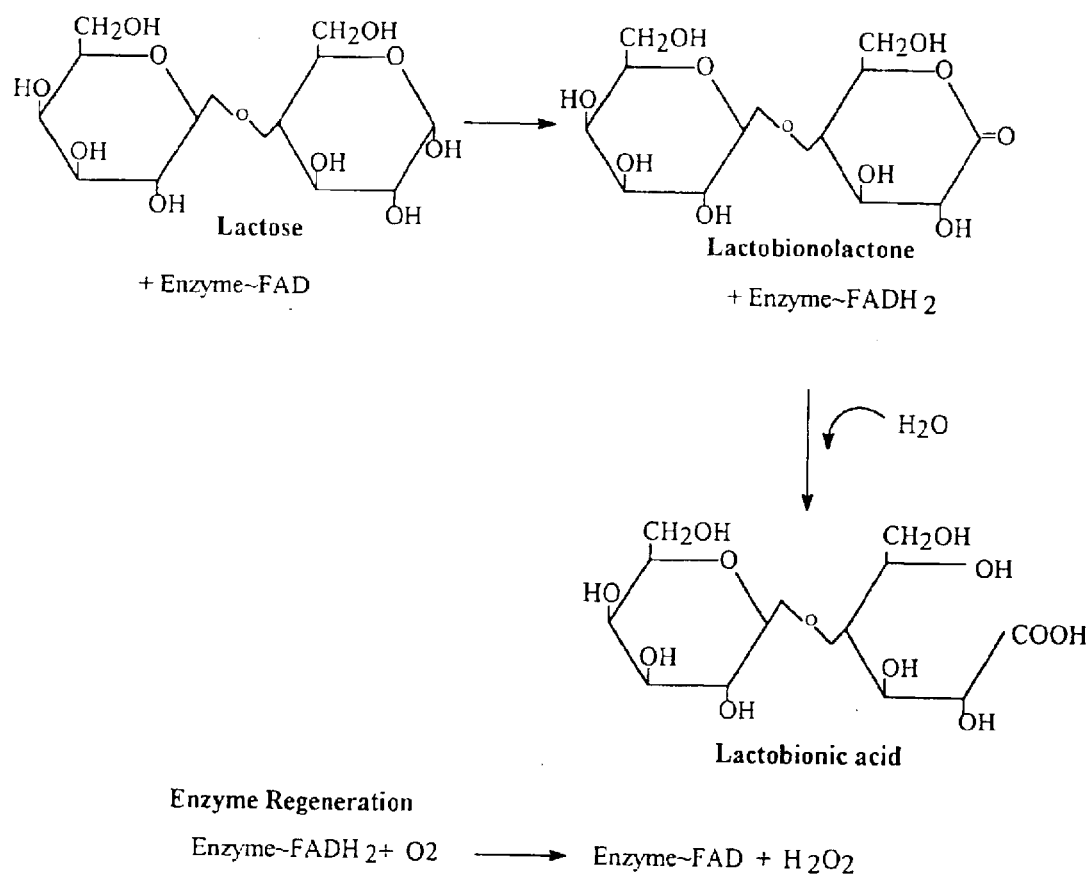
FIG. 7 is a reaction flow scheme showing a theorized reaction mechanism for the enzymatic oxidation of lactose using lactose oxidase.

A particularly suitable enzyme for lactose oxidation has been developed by Novozymes A/S and is described in Patent WO 9931990, which is hereby incorporated by reference. As illustrated in FIG. 7, the lactose oxidase can be introduced and used in the form of a flavo-enzyme. This flavo-enzyme from Novozymes A/S contains flavin adenine dinucleotide (FAD) and, thus, does not require an external electron acceptor or a second enzyme to regenerate the cofactor. This carbohydrate oxidase is produced in a genetically modified microorganism. FAD (flavin adenine dinucleotide) is used as a electron-transfer co-factor with the carbohydrate oxidase enzyme. The enzyme includes activity between a pH of about 5 to about 9, and at temperatures including up to approximately 100° F. (88° C.). The preferred substrates are di, tri, and tetrasaccharides. Among the disaccharides, lactose is the most suitable substrate; oxidation at the C1 position of the glucose moiety of lactose results in lactobionic acid and hydrogen peroxide formation in a single reaction step. This enzyme will generally be referred to as "lactose oxidase." The activity units value is 146 U/ml, measured as mMole oxidized glucose per minute at pH 6 and 77° F. (25° C.). As shown in the reaction pathway schematically illustrated in FIG. 7, FAD is reduced in an intermediate form and then is deoxidized upon completion of the conversion of the lactose to lactobionic acid. Hydrogen peroxide is a by-product of the reaction.

Cellobiose dehydrogenase is also a useful enzyme for converting lactose to lactobionic acid. Canevascini et al., *Zeitschrift fur Lebensmittel Untersuchung und Forschung*, 175: 125–129 (1982). This enzyme is, however, complex and requires the use of a relatively expensive co-factor (e.g., quinones, cytochrome C, Fe(III), and the like); it also requires immobilization. Also, a second enzyme, laccase, is required to regenerate the co-factor used with cellobiose dehydrogenase. The use of glucose-fructose oxidoreductase to oxidize lactose results in two products, sorbitol and lactobionic acid, and a further separation procedure is necessary to recover the lactobionic acid product. Nidetzky et al., *Biotechnology and Bioengineering*, Vol. 53 (1997). Nonetheless, glucose-fructose oxidoreductase also is a suitable enzyme for the practice of this embodiment of the invention. Alternatively less efficient enzyme systems can be used. For example, lactase can be used to first hydrolyze the lactose to glucose and galactose followed by oxidation of glucose and galactose using glucose oxidase and galactose dehydrogenase.

The amount of oxidase enzyme added is an amount effective to reduce the pH or help reduce the pH of the cheese mix such that it coagulates. The amount of oxidase addition preferably is sufficient to generate a lactobionic acid content in the cheese mix of from about 0.1 to about 10 percent, particularly from about 2 to about 6 percent, and more particularly from about 3 to about 5 percent, based on the total weight of the cheese mix before separation of curd and whey.

A lactic acid culture also can be added in step 207. As the lactic acid culture also has the effect of converting lactose to lactic acid and reducing the pH of the cheese mix, the amount of lactose oxidase added can be adjusted downward to a relatively smaller amount to accommodate any addition of culture in this regard.

Referring still to FIG. 2, in step 209, the cheese mix is then incubated at about 72° F. for about 12 to about 20 hours. This incubation period, or fermentation, is allowed to continue until the pH of the cheese mix is about 4.5 to about 4.6. This is followed by heating to 180° F. to inactivate any culture added (step 211). After homogenization (step 213), the cream cheese curd (217) is separated from the whey (219).

In experimental studies, such as described below, the addition of carbohydrate oxidase permits the use of higher lactose levels or increases the amount of the lactose-derived solids in the dairy liquid ingredients that are converted to lactobionic acid, as compared to controls prepared with cultures but not the oxidase. The amount of lactose conversion achieved in the dairy liquid ingredients in this embodiment can reach about 85 percent or more. This permits cheeses to be prepared having highly reduced lactose content, or, alternatively, higher lactose content dairy ingredients can be used in the cheese mix.

Figure 3:
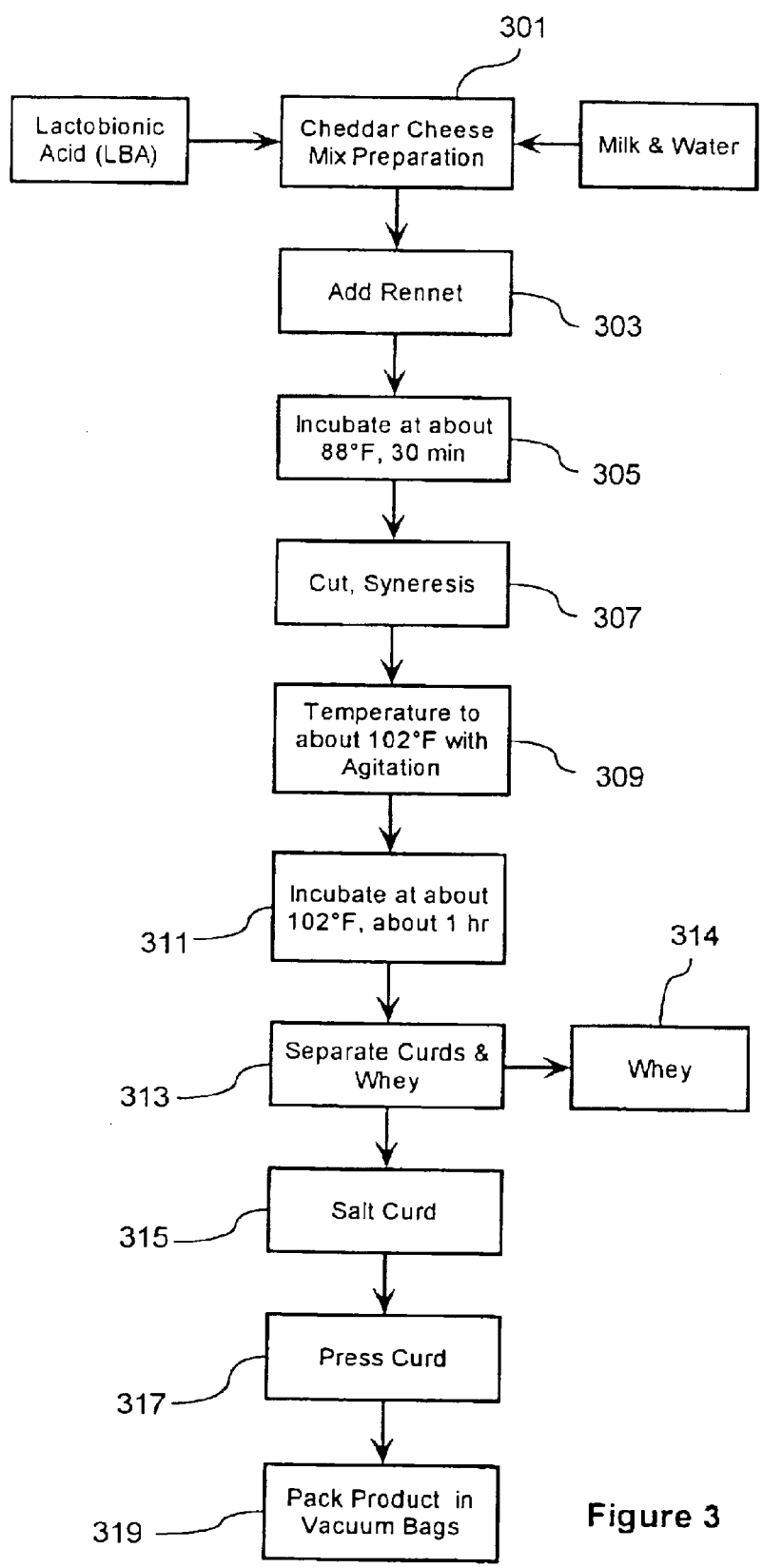
FIG. 3 is a flow chart of steps used in an embodiment of the invention for production of cheddar cheese.

Referring to FIG. 3, another embodiment of the invention is illustrated in which lactobionic acid is used as an active ingredient in a cheddar cheese mix. Furthermore, in this illustration, lactic acid bacteria, or other culture, is completely omitted, such that the cheese mix is directly acidified using lactobionic acid alone in step 301. The cheese mix is prepared by mixing whole milk, water, and lactobionic acid in amounts generally as described relative to the discussion of FIG. 1. Next rennet (e.g., chymosin) is added and the mixture is incubated at about 88° F. for about 30 minutes. The coagulum is cut with a knife to permit syneresis (step 307). The temperature is increased to about 102° F. with agitation and held for about 60 minutes. The pH of the coagulum can be about 5.8 at this point. The whey (314) is removed from the curd (step 313), followed by salting (315), pressing (317), and packing the cheese curd (319). The whey by-product (314) contains lactobionic acid and can be reused as a starting ingredient in cheese production.

As to the renneting in step (303), the most common method of enzyme coagulation is proteolysis by aspartate proteinases, which are enzymes that hydrolyze proteins. The main source of these enzymes is rennet, which can be obtained from animal, plant, or fungal sources. The active ingredient of rennet is the enzyme fraction called rennin. The most important rennet is chymosin. The traditional main source of rennet has been the abomasum of young calves, but presently chymosin is commercially produced from genetically altered-micro-organisms.

The cheddar cheese product made with and containing lactobionic acid has satisfactory organoleptic and textural attributes without any off-flavors, and it is comparable to conventional cheddar cheese in terms of these characteristics. This embodiment, while illustrated with respect to cheddar cheese, is also applicable to the production of other hard cheeses.

Figure 4:
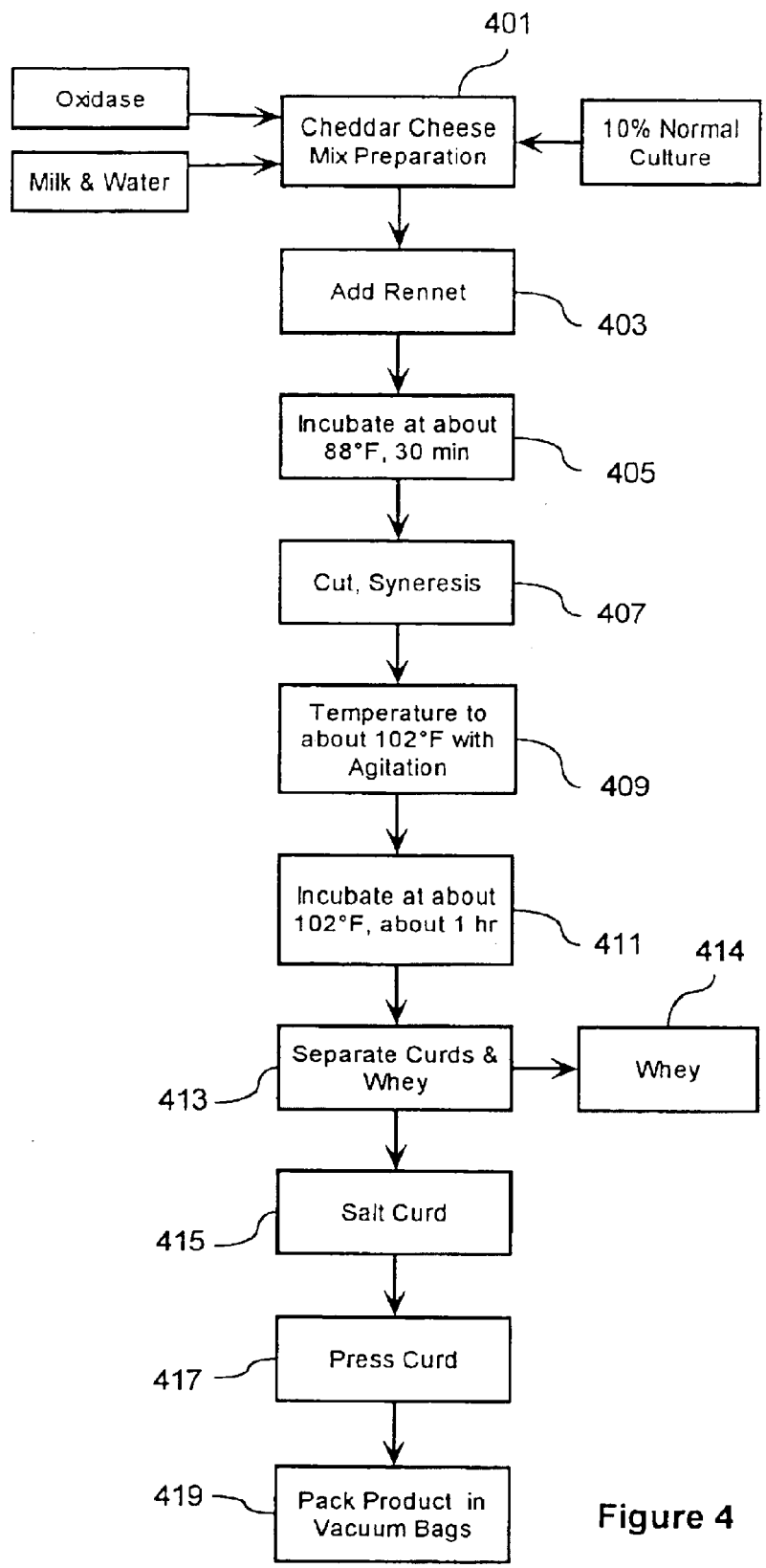
FIG. 4 is a flow chart of steps used in another embodiment of the invention for production of cheddar cheese.

Referring to FIG. 4, this embodiment is a variation on the embodiment of FIG. 3 in that the lactose oxidase is used to partially replace cultures to aid acidification of cheddar cheese. In step 401, the cheddar cheese mix is prepared with only about 10 percent of the conventional amount of culturing (i.e., about 0.001 percent culture). An oxidase enzyme, such as lactose oxidase, is also added to the cheese mix. The function and amount of lactose oxidase added here are similar to that described above relative to the embodiment described in connection with FIG. 2. Thereafter, steps 403–419 are performed which are similar to steps 303–319 described in relation to FIG. 3.

The cheddar cheese product had satisfactory organoleptic and textural attributes without any off-flavors, and it is comparable to conventional cheddar cheese in terms of these characteristics. The oxidase converts a significant portion of the original lactose content of the dairy ingredient (e.g., milk) to lactobionic acid, which also helps to acidify the mix. Generally, about 10 to about 50 percent of the lactose can be converted to lactobionic acid; more preferably, about 20 to about 40 percent is converted.

Figure 5:
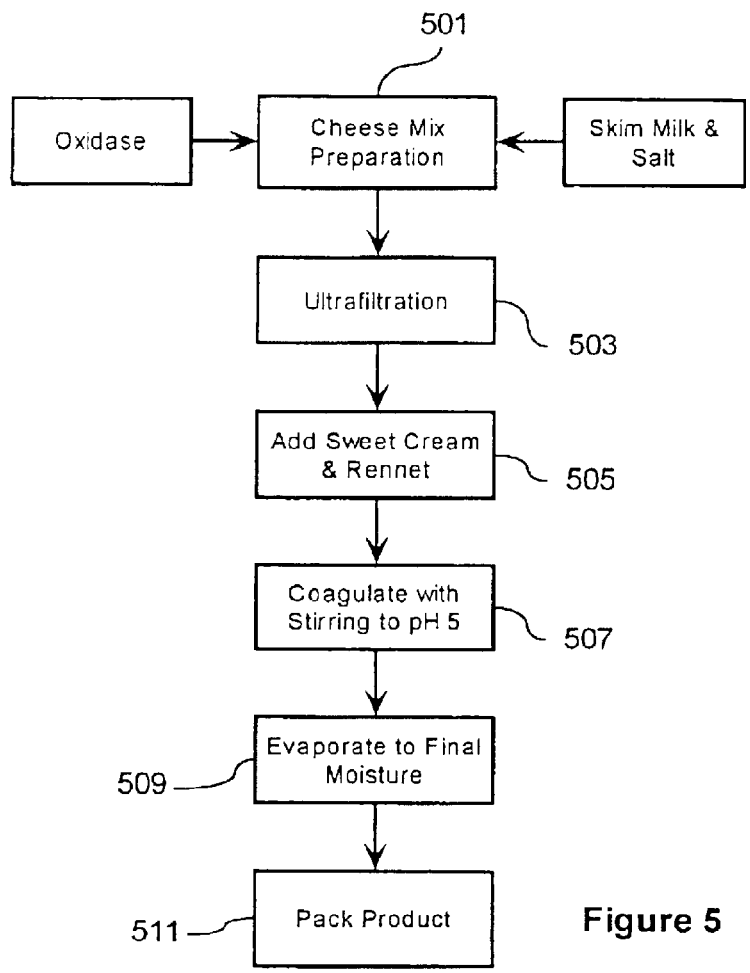
FIG. 5 is a flow chart of steps used in an embodiment of the invention for production of UF cheese.

Referring now to FIG. 5, oxidase enzyme generation of lactobionic acid in situ for direct acidification of membrane filtered cheese in lieu of culturing is illustrated according to another embodiment of the invention. The UF cheese mix is prepared including an oxidase (step 501). Useful oxidases in this regard include those such as described above relative to the discussion of FIG. 2. Whole milk is ultrafiltered or microfiltered using a conventional apparatus for this purposes (step 503). Milk is cycled across a semi-permeable membrane at an elevated pressure such that water and low molecular weight components pass through the membrane, while certain proteins and fats are retained by the membrane. The semi-permeable membrane, for example, can be selected to restrict passage of molecules having a molecular weight larger than about 10,000. In step 505, sweet cream and rennet are added, followed by coagulation (step 507), and evaporation (step 509) to form the product 511 which is then packed.

The lactose oxidase is added in an amount effective to oxidize at least a portion of the lactose to lactobionic acid, and to reduce the pH of the cheese mix sufficiently that a separately added rennet can induce coagulation. Generally the amount of oxidase added is sufficient to oxidize at least about 10 percent of the lactose present, more preferably about 10 to 95 percent of the lactose present, and even more preferably about 20 to about 40 percent of the lactose present.

The use of such an oxidase to generate lactobionic acid in situ using lactose present in the mixture offers the added advantage of significantly reducing lactose levels in the manufactured cheese or other dairy products as compared to those otherwise present in the absence of oxidase addition, all other things equal. Again, this permits attainment of either lower lactose levels in the cheese or other dairy product or the ability to use dairy ingredients in the cheese mix having higher lactose levels than otherwise would be ordinarily used. The lactobionic acid also serves to displace and diminish starter culture requirements, either partly or fully, otherwise applicable to cheese manufacture, while maintaining adequate texture and without the appearance of off-flavors. Where only part of the culturing is replaced with lactobionic acid introduction, the coagulation of the cheese mix can be performed via acid coagulation alone using both lactic acid and lactobionic acid added in a combined amount. In this way, yields are improved as time savings are achieved by at least reducing the culturing requirements. The optional co-addition of flavor concentrate to the cheese mix including the lactobionic acid can be used to adequately compensate in flavor for any reduced or omitted starter culture usage insofar as any desired cultured notes.

Figure 6A:
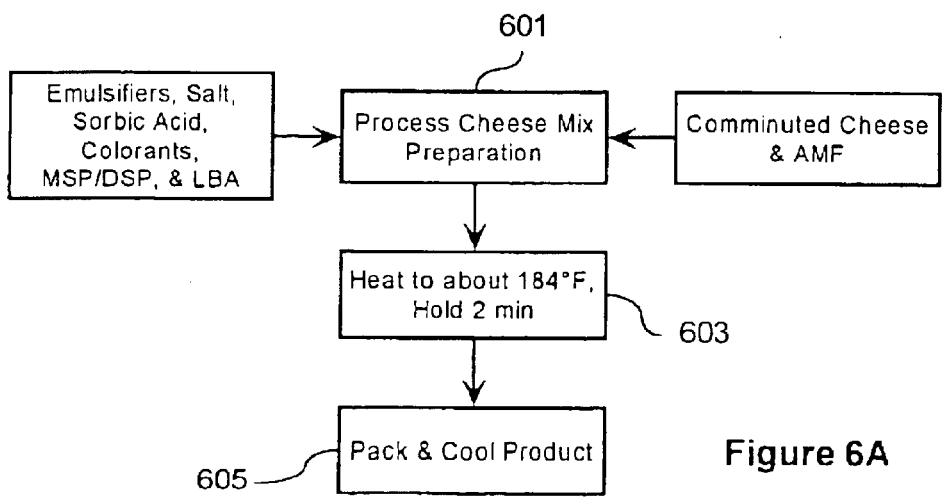
FIG. 6 contains flow charts of steps used in embodiments of the invention for production of process cheese wherein lactobionic acid from various sources (6A, 6B, and 6C) is added to a process cheese mixture.
Figure 6B:
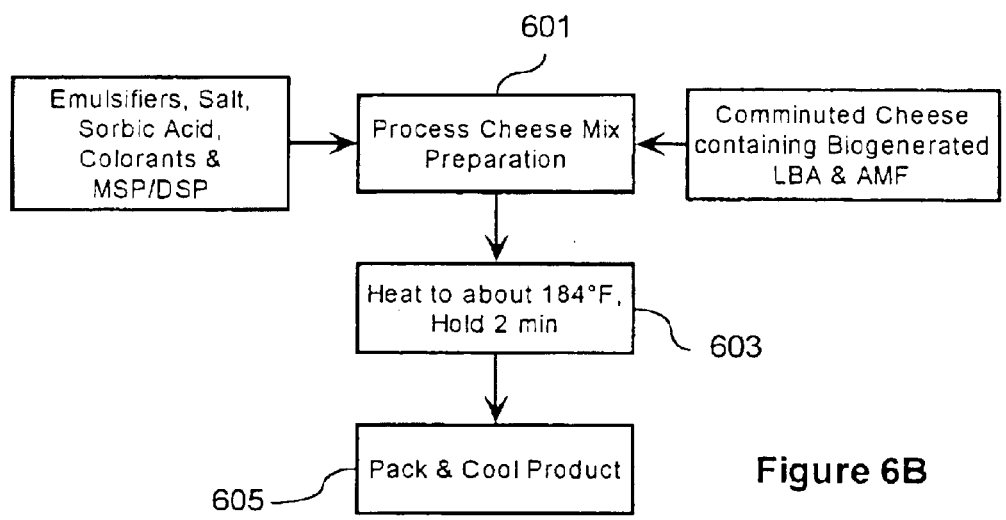
Figure 6C:
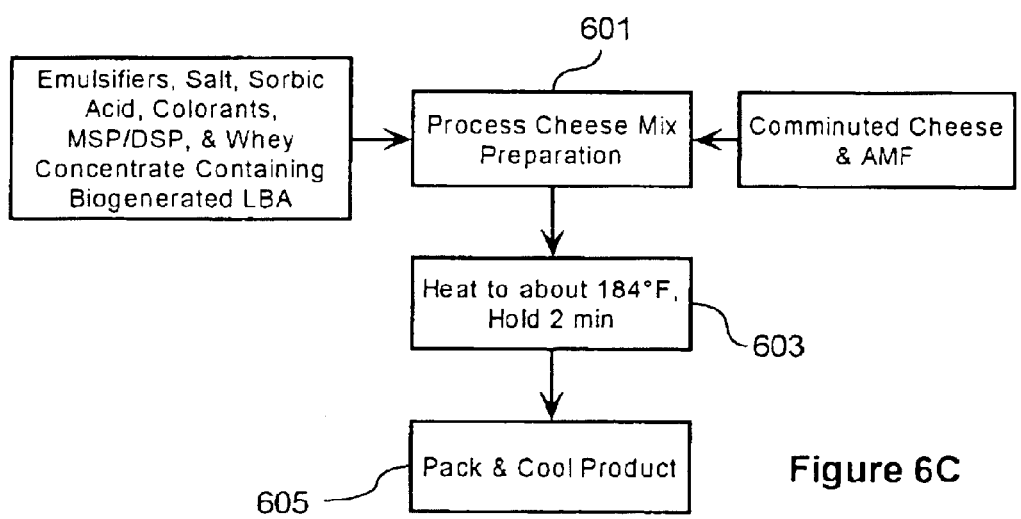

In an important embodiment of the present invention, lactobionic acid is incorporated into process cheese. Referring to FIG. 6, lactobionic acid, in various forms, is added to a process cheese mix otherwise including conventional ingredients such as emulsifiers, salt, preservative, colorants, comminuted hard cheese, and dairy components such as whey protein concentrates and dry whey (step 601). The cheese mix is heated to a plastic homogenous mass (step 603), and then is packed and cooled (step 605). In FIG. 6A, the lactobionic acid is added directly to the process cheese mix preparation. In FIG. 6B, the lactobionic acid is added using cheese containing biogenerated lactobionic acid. And in FIG. 6C, the lactobionic acid is added using whey or whey concentrate or permeate containing biogenerated lactobionic acid. Such whey concentrate could be obtained, for example, by treating whey with an appropriate lactose oxidase. The process cheese product made with and containing lactobionic acid has satisfactory organoleptic and textural attributes without any off-flavors, and it is comparable to conventional process cheese in terms of these characteristics.

In the production of process cheese, it is often desired to reduce the fat and/or dry matter content of the process cheese. This need is based, inter alia, on consumer preferences for low calorie products and attempts to save costs per unit amount of process cheese. If either the fat or dry matter content in process cheese is reduced, however, there is often a problem concerning the texture of the resulting reduced fat and/or dry matter content product. Namely, such a product will usually have a degraded texture and fail in the sensory evaluation (i.e., mouthfeel). The addition of lactobionic acid and/or a salt thereof to process has been found to provide a process cheese capable of having a reduced fat and/or dry matter content while preserving the texture and the sensory characteristics associated therewith. Specifically, it has been found that lactobionic acid or a salt thereof enhances process cheese post-creaming behavior (i.e., it increases the hot cheese viscosity during creaming following a heat treatment of the process cheese formulation). Lactobionic acid was found to be effective in enhancing process cheese post-creaming (i.e., increasing the hot cheese viscosity (or maintaining it at a reduced fat and/or dry matter content)), but not delaying the creaming process. Many firming agents (e.g., dextran, locust bean gum, and the like) also increase the hot cheese viscosity during creaming, but generally result in delaying the entire creaming process. Furthermore, gums and starches lead to negative sensory attributes (e.g., mouthfeel and surface gloss) even at amounts of less than 2 percent. Gums, for example, cannot be used in some process cheese spreads at all for that reason.

Accordingly, the present invention provides a process cheese comprising about 0.1 to about 10 percent of lactobionic acid and/or a salt thereof. Preferably, the amount of lactobionic acid or a salt thereof in the process cheese of the present invention is in the range of from about 0.5 to about 7 percent, and more preferably about 1 to about 5 percent.

The lactobionic acid may be introduced into the process cheese formulation as such or in the form of its salt or mixtures thereof. Any salt may be used as long as it is acceptable in a food product and does not otherwise deteriorate the process cheese characteristics. Examples of respective salts are alkali and earth alkali metal salts such as sodium, potassium, calcium, and magnesium salts as well as ammonium salts. Among these salts, sodium and calcium salts are preferred.

The dry matter content in the process cheese of the invention preferably amounts to about 25 to about 60 percent, and more preferably about 30 to about 50 percent. The fat content in the process cheese according to the present invention is preferably about 5 to about 40 percent, and more preferably about 7 to about 30 percent. In this context, the expression "reduced fat and/or dry matter content" is to be understood as relating to a corresponding cheese formulation which does not contain lactobionic acid. Accordingly, the person skilled in the art will appreciate that there may be process cheese formulations without lactobionic acid and having a lower fat and/or dry matter content than a process cheese according to the present invention. However, those conventional process cheese formulations will consequently lack the characteristics of the corresponding process cheese of the invention, such as textural stability and sensory benefits.

A process cheese of the present invention, including one having a reduced fat and/or dry matter content, may be produced by mixing conventional process cheese formulation ingredients with lactobionic acid and/or a salt thereof. Ingredients conventionally used in the manufacture of process cheese comprise cheese, butter, anhydrous milk fat, casein, skim milk powder, whey powder, carbohydrates (such as starch, lactose, lactic acid and binding agent), salts (such as sodium chloride and melting or emulsifying salts (e.g., salts of citric and phosphoric acids)) and water. That is, conventionally used process cheese formulations may be employed in the process of the present invention.

In the process of the invention, the lactobionic acid is preferably added in the form of an aqueous solution wherein the acid is introduced as such or in the form of its salt. A salt of lactobionic acid may be formed by adding a base such as sodium hydroxide, potassium hydroxide, magnesium hydroxide or calcium hydroxide or the respective carbonates to a solution of lactobionic acid. The salt may also be formed by adjusting the pH in the process cheese formulation. Thus, it is to be understood that normally lactobionic acid salt will be formed upon mixing of the process cheese formulation ingredients with lactobionic acid. Preferably, the pH of the resulting process cheese formulation is adjusted in the range of about 5.5 to about 5.9, more preferably about 5.6 to about 5.8.

In a preferred embodiment of the process of the present invention for preparing process cheese, the lactobionic acid and/or its salt partially or fully replaces lactose in the process cheese formulation. An additional benefit of the invention is that browning due to the Maillard reaction is not increased in formulations with maintained lactose level and drastically reduced in formulations where lactose is partially replaced by lactobionic acid or its salt.

In the mixing step of the process according to the present invention, any mixing procedure practiced in the manufacture of process cheese can be used. Typically, this is a mixing to homogeneity under stirring/shear conditions at temperatures between about 15 and about 30° C., and more preferred between about 20 and about 25° C. Conventional mixing equipment may be used such as any type of blender (e.g., stirrer, single or double ribbon, and the like). The mixing step as such will result in the desired texture (i.e., gel-like paste); the resulting product can be packaged as the final product or it may be treated further if desired or necessary depending on relevant government regulations. For example, an UHT (ultra high temperature) treatment is legally required in certain countries or regions (e.g., European Union) to ensure a reduction of specific microorganisms (e.g., Clostridia). The structure of the process cheese mixture will usually be destroyed in a heat treatment step yielding a solution of highly hydrated ingredients regardless of the particular mixing device or procedure applied. Such a treatment will normally require a subsequent post-creaming of the mixture to regain the desired textural properties (i.e., a firm gel structure). Process cheese that does not undergo such a texture-destroying treatment, such as in the United States, generally are not post-creamed.

A detailed process for preparing process cheese with a post-creaming procedure will now be described. If the resulting mixture of process cheese formulation ingredients and lactobionic acid or its salt is heat treated, this treatment can be carried out under conditions commonly employed in the sterilization or UHT treatment. That is, the temperature is preferably about 105 to about 150° C. If the heat treatment is a UHT treatment, the temperature is more preferably about 135 to about 140° C. (in case of indirect heating, e.g., with a plate heat exchanger) or about 140 to about 150° C. (in case of direct heating, e.g., by steam injection). If the heat treatment is a sterilization treatment, a more preferred temperature is in the range of about 110 to about 120° C. The heat treatment is preferably carried out for about 2 seconds to about 20 minutes. More preferably, in case of the UHT treatment, the heating time is from about 2 to about 15 seconds, whereas it is in the range of from about 10 to about 20 minutes for the sterilization treatment. In general, the heat treatment can be carried out by means of direct steam injection or by using a scraped surface heat exchanger or any type of batch cooker (e.g., Stephan cooker) as conventionally used in this art.

In case of heat treatment, the heat-treated mixture is subsequently cooled to a temperature of preferably below about 100° C. and above about 15° C. (e.g., about 25 to about 98° C.). Economically sensible is of course a temperature that is close to that one of the following post-creaming step. Therefore, a particularly preferred range is about 70 to about 95° C. The cooling may be carried out by flash cooling (by pressure release) or by using any type of heat exchanger or other cooling device such as a plate heat exchanger, scraped surface heat exchanger, and the like, or any combination thereof.

Figure 8:
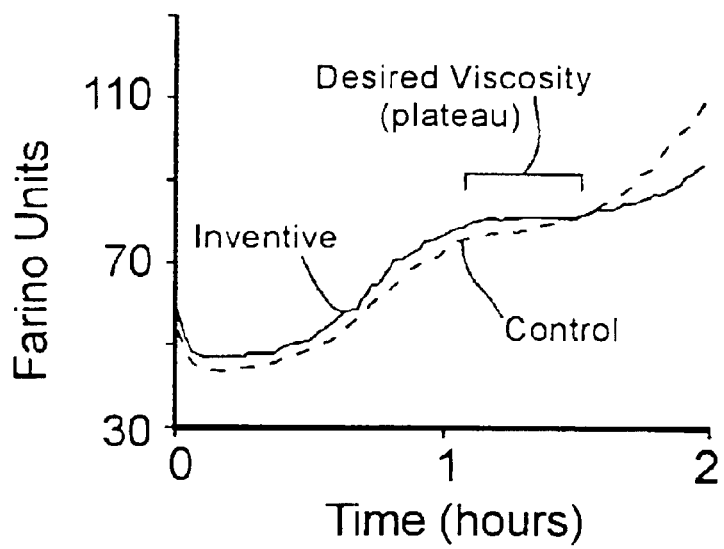
FIG. 8 is a graph showing post-creaming curves (viscosity as a function of time) for the process cheeses (inventive and control) as prepared in Example 7.
Figure 9:
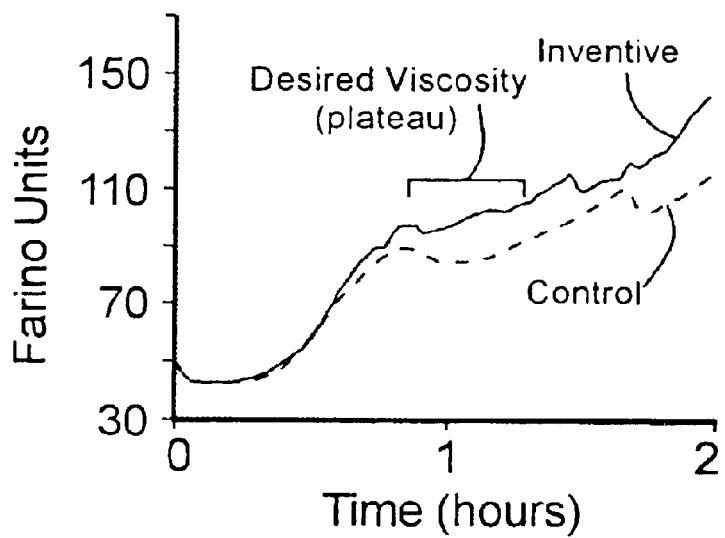
FIG. 9 is a graph showing post-creaming curves (viscosity as a function of time) for the process cheeses (inventive and control) as prepared in Example 8.

Next, the cooled mixture is subjected to post-creaming which is preferably carried out at a temperature from about 70 to about 95° C., and more preferably about 80 to about 85° C. The post-creaming treatment can be carried out in any conventional vessel or tank with a device that allows a gentle, smooth stirring/shearing action. The post-creaming treatment is preferably conducted until the viscosity level of a corresponding process cheese not containing lactobionic acid or its salt is achieved. Time-dependent viscosity curves of conventional post-creaming procedures are shown in FIGS. 8 and 9. As is evident from these curves, after an initiation phase, the viscosity reaches a plateau; preferably, the post-creaming treatment is continued until this plateau is reached. For purposes of this invention, this plateau is considered to be the "time-independent viscosity level."

Although it may be desirable for better process monitoring, it is not necessary to measure the viscosity or related parameter in order to benefit from the effect of the invention. A few test trials and the evaluation of the corresponding product texture may be sufficient to quickly identify the optimum creaming time (which will usually be at the plateau) for a formulation containing lactobionic acid or its salt. A plant manufacture can then be run with a time identified this way. The period of the post-creaming treatment is preferably up to about 90 minutes, and more preferably about 10 to about 40 minutes. The shear rate employed in the postcreaming treatment will usually affect the creaming time and will vary depending on the plant layout (e.g., size, continuous or batch operation, and the like). However, characteristics such as shear rate do not have to be used as a controlling parameter.

In a preferred embodiment of the process of the present invention, the postcreaming reaction is initiated ("catalyzed") by adding well-creamed finished product (i.e., pre-cooked cheese) in an amount of up to about 10 percent, preferably more than about 0.1 percent, more preferably in the range of from about 0.5 to about 5 percent, and most preferably about 2 percent. The pre-cooked cheese may be an ad hoc prepared material or, as in Examples 8 and 9, a commercial product. In the plant, it may be convenient to use rework as the pre-cooked cheese for initiating the post-creaming reaction. The amount of pre-cooked cheese will affect the creaming time to a certain extent (i.e., the more pre-cooked cheese the shorter the creaming time); in Examples 8 and 9, portions of a creamed commercial product served this purpose. The addition of such a "catalyst" (i.e., pre-cooked cheese) is important to achieve the short creaming times in the Examples 8 and 9. If no pre-cooked cheese is used, the post-creaming usually takes considerably longer (e.g., sometimes twice as long). FIGS. 8 and 9 are graphs showing the post-creaming curves (i.e., viscosity as a function of time) for the samples described in Examples 7 and 8, respectively.

The heat-treated and post-creamed process cheese may be further treated in the conventional manner (e.g., cooled, packaged, stored). The resulting process cheese is beneficial over conventional products in that it preserves comparable texture and sensory attributes at a lower fat and/or dry matter content or, alternatively, excels when exhibiting the same fat and dry matter content.

Having generally described the embodiments of the process illustrated in the figures as well as other embodiments, the invention will now be described using specific examples which further illustrate various features of the present invention but are not intended to limit the scope of the invention, which is defined in the appended claims. All percentages used herein are by weight, unless otherwise indicated.

EXAMPLE 1

An experimental composition incorporating features of one embodiment of the invention was prepared to demonstrate the use of lactobionic acid for direct acidification in the manufacture of cream cheese. The composition of the cheese mix prepared in this regard is presented in Table 1.

In order to prepare the cream cheese mixture, the lactobionic acid, commercially obtained from Lonza Inc. (Fairlawn, N.J.) as a white crystalline powder, was dissolved with stirring in the water used in the composition. The lactobionic acid was added in its free acid form in this experiment. The lactobionic acid-containing solution then was blended with the rest of the ingredients comprised of the sweet cream, ultrafiltered milk, salt (NaCl), and gum carob. The blend coagulated and the pH of the resulting mix was about 4.52. The blend was then cooked to about 180° F., and then homogenized at about 2500 psi. Throughout this process, the liquid dairy component was not permitted to cool to below about 140° F. The cream cheese product obtained was then packaged in individual eight ounce cups and stored cold.

TABLE 1

Ingredients of an inventive cream cheese composition.

| Component | Amount (%) |
| --- | --- |
| sweet cream | 77.89 |
| UF milk (5X) | 17.0 |
| lactobionic acid | 4.0 |
| salt | 0.7 |
| gum | 0.3 |
| potassium sorbate | 0.03 |
| flavorants | 0.08 |

The cream cheese product was organoleptically evaluated by trained evaluators. No off-flavors were detected. The overall appearance, taste, texture, and mouthfeel were acceptable. Also, the lack of cultured notes in the directly acidified cream cheese obtained could be overcome by using flavoring systems for creating a desired cream cheese flavor.

EXAMPLE 2

An experimental composition incorporating features of another embodiment of the invention was prepared to demonstrate the use of lactose oxidase enzyme to generate lactobionic acid in situ for acidification of cream cheese. The composition of the cream cheese mix is presented in Table 2. This composition was compared with a control composition representative of a conventional cream cheese.

In this experiment, an enzyme ingredient, lactose oxidase, was used to generate lactobionic acid in situ during the production of the cream cheese. The lactose oxidase was obtained from Novozymes A/S (Franklinton, N.C.). This lactose oxidase was a flavo-enzyme having FAD (flavin adenine dinucleotide) present as co-factor with the lactose oxidase.

In order to prepare the cream cheese mix, the sweet cream, WPC 80, salt, gum carob, cream cheese flavor concentrate, and K sorbate were blended. The blend was then cooked to about 180° F. by heating and held for about 5 minutes, followed by homogenization of the cooked blend at about 2500 psi. At this juncture, the homogenized mix was inoculated with the lactose oxidase enzyme and a bulk cream cheese starter culture. The starter culture was a commercially available DVS Lactococcus lactis culture obtained from Chris Hansen, Inc., Milwaukee, Wis. After incubating at about 72° F. overnight (about 16 hours), the pH had dropped to about 4.4. After adjusting the pH to about 4.7 using fresh uninoculated cream cheese mix, the mixture was then subjected to a heating step at about 180° F. and homogenized at about 2500 psi. The cheese product obtained was then packaged in 8 ounce cups and stored cold.

As a control run, another cheese mix was prepared according to the formulation described in Table 2 and the procedure described above, except that it omitted the lactose oxidase ingredient. The mixing percentages of the control run also are presented in Table 2.

TABLE 2

Ingredients of inventive and control cream cheese compositions.

| Ingredient | Inventive Sample Amount (%) | Control Sample Amount (%) |
| --- | --- | --- |
| sweet cream | 77.83 | 79.41 |
| water | 3.23 | 2.43 |
| UF milk (5X) | 17.0 | 17.0 |
| lactose oxidase (258 U/ml) | 0.82 | 0 |
| culture | 0.01 | 0.01 |
| salt | 0.70 | 0.73 |
| gum | 0.30 | 0.31 |
| potassium sorbate | 0.03 | 0.03 |
| flavorants | 0.08 | 0.08 |

The untreated control cream cheese product was determined to contain about 2.5 percent lactose. By contrast, the lactose oxidase enzyme-treated cream cheese product representative of the invention contained only about 0.3 percent lactose. The lactobionic acid content of the cream cheese products was determined using high performance liquid chromatography using an ion exchange protocol. In the case of the lactose oxidase enzyme-treated product, about 88 percent of the original lactose had been converted to lactobionic acid.

As also shown by these results, this invention permits and enables the use of higher lactose containing whey protein concentrates in cream cheese mix formulations in addition to in situ generation of acidity to aid acidification.

EXAMPLE 3

An experimental composition incorporating features of yet another embodiment of the invention was prepared to demonstrate the use of lactobionic acid for direct acidification in the manufacture of cheddar cheese.

A cheddar cheese mixture containing 20 g lactobionic acid dissolved in 475 ml milk and 5 ml water was prepared in a sterile beaker. 500 µL double strength CHY-MAX™ was then added to the mixture. CHY-MAX™ is a range of fermentation produced chymosin products, and it was obtained from Chr. Hansen, Inc., Milwaukee, Wis. The resulting mixture was incubated at about 88° F. for about 30 minutes. The coagulum was cut with a knife to allow syneresis. The coagulum was cooked to increase its temperature from about 88° F. to about 102° F. with frequent shaking in a water bath. Once the coagulum reached about 102° F,. it was incubated for about an additional 60 minutes at a pH of about 5.8, decanted, and then pressed to remove whey. The curd was salted with 0.7 percent sodium chloride. The salted curd was pressed overnight (i.e., about 16 hours), and then the cheese was packed in vacuum bags.

The cheddar cheese product had satisfactory organoleptic and textural attributes without any off-flavors being detected. This embodiment offers time savings in hard cheese production, and thus increased output yields, due to the elimination of processing involving lactic acid bacterial cultures.

EXAMPLE 4

An experimental composition incorporating features of another embodiment of the invention related to the manufacture of hard cheeses was prepared to demonstrate the use of lactose oxidase to partially replace cultures, to aid acidification in cheddar cheese making.

In order to prepare the cheddar cheese mixture, 950 units of lactose oxidase of the same type as that described in Example 2, was added to 475 ml milk and 5 ml water in a sterile beaker with mixing along with 0.001 percent starter culture. The starter culture was a DVS Lactococcus lactis culture, supplied by Chris Hansen, Inc., Milwaukee, Wis. The amount of culture normally used in cheddar cheese making is about 0.01 percent of the cheese mix, so this example employed only about 10 percent of the typical amount of starter culture content in a cheese mix.

Then, 500 µL of double strength CHY-MAX™ was added, and the resulting blend was incubated at about 88° F. for about 30 minutes. The coagulum was cut with a knife to allow syneresis. The coagulum was cooked to increase its temperature from about 88° F. to about 102° F. with frequent shaking in a water bath. Once the coagulum reached about 102° F., it was incubated for an additional 60 minutes at pH 5.8, decanted, and then pressed to remove whey. The curd was salted with 0.7 percent sodium chloride. The salted curd was pressed overnight (i.e., about 16 hours), and then the cheese was packed in vacuum bags.

The results demonstrated that the in situ production of the lactobionic acid in cheddar cheese prepared in this experiment according to an embodiment of the invention reduced the amount of culture needed to be added to the cheese mix to lower the pH as needed.

Also, the lactose oxidase enzyme-treated cheddar cheese product representative of the invention contained less than about 0.2 percent lactose. A separate control run of the cheddar cheese product, prepared in the same way except using 0.01 percent starter culture and without the lactose oxidase ingredient, was determined to contain less than about 0.3 percent lactose. The cheddar cheese product had satisfactory organoleptic and textural attributes without any off-flavors, and it was comparable to the control sample of cheddar cheese in terms of these characteristics.

EXAMPLE 5

In another experiment, a lactose oxidase enzyme was used to generate lactobionic acid in situ for acidification in the production of UF cheese in lieu of culturing. The composition of the UF cheese mix is presented in Table 3.

For this procedure, 1000 ml of fresh skim milk was concentrated up to about five times at about 145° F. using a ultrafiltration device having a membrane pore size which restricted passage of molecules larger than 10,000 molecular weight. Prior to starting ultrafiltration, a lactose oxidase enzyme of the same type described in Example 2 was added in an amount of 0.2 units per gram of milk. 5.4 g of salt also was added at this time. Concentration was completed by the ultrafiltration procedure when 80 percent of the original milk volume was removed. 103 g of sweet cream (40 percent) was then added to the concentrated milk to achieve a protein to fat ratio of about 0.8. 10 µL of rennet was added to the concentrated skim milk/cream mixture, and the mixture was stirred slowly until the lactose oxidase enzyme had converted sufficient lactose to lactobionic acid such that the mixture to reached a pH of about 5. Evaporation was performed to reach the final desired cheese moisture level by a conventional evaporation method used for purpose.

TABLE 3

Ingredients of an inventive UF cheese composition.

| Ingredient | Amount |
| --- | --- |
| skim milk | 1000 ml |
| sweet cream (40%) | 103 g |
| enzyme | 2000 units |
| salt | 5.4 g |
| rennet | 10 µL |

By determining the lactose content in the product UF cheese and comparing that value with that of a control run, in which the UF cheese was prepared in the same manner except omitting the addition of the lactose oxidase, it was confirmed that the lactose present in the skim milk was converted into lactobionic acid when processed in the presence of the lactose oxidase enzyme. Additionally, less diafiltration was needed for the reacted retentate, as compared to that typically used in conventional UF cheese production, because of the conversion of lactose to lactobionic acid. That is, this embodiment captured much more lactose derived solids than the same process would using starter cultures. Since lactobionic acid (formula weight 358.3) has a mass weight/mole that is about four times the mass weight/mole of lactic acid (formula weight 90.08), on a molar basis, a greater mass derived from lactose is therefore retained on an equimolar basis when lactose is converted to lactobionic acid, such as according to this embodiment of the invention, rather than to lactic acid.

EXAMPLE 6

In this experiment, process cheeses were prepared from cheese mix compositions containing one of three different forms of lactobionic acid. The basic compositions of the three process cheese mixes are presented in Table 4. They only varied as to the particular form of the lactobionic acid used. As a control run, another cheese mix was prepared according to the formulation described in Table 4 and the procedure described below, except that it omitted the lactobionic acid.

The cheese mixes representing this invention comprised the following ingredients: whey protein concentrate (WPC 34, Wisconsin Whey International, Juda, Wis.) containing 34 percent whey protein, milk protein concentrate (NZ MPC-70, New Zealand Milk Products, Wellington, New Zealand), dry whey (containing 71.78 percent lactose; Krafen, Kraft Foods, Glenview Ill.), water, comminuted cheese, anhydrous milk fat (AMF), the colorants APO and annatto, sorbic acid, emulsifying agents (i.e., monosodium phosphate and disodium phosphate), salt (NaCl), condensate, and lactobionic acid. The condensate is the water added into the cheese mass during cooking by way of condensation of steam used in the direct steam injection process used in the process cheese manufacture. The amount of condensate is dependent upon the time, temperature of cooking, and initial temperature of the cheese mix. This amount is determined and is used in adjusting the water in the formulation. The control run had the same composition except that it did not contain lactobionic acid (all other components were included using the same ratios).

The cheese making procedure was as follows. Cheese, AMF, emulsifying salt, sorbic acid, mono and disodium phosphate, APO and annatto were added to a Hobart blender bowl and blended for about 2 minutes. A wet blend of the rest of the ingredients was made in the lactobionic acid solution (described below) and added to the blender bowl. Mixing was continued until all the components were well blended. For the control run, a wet blend of the rest of the ingredients was instead made in the water without the lactobionic acid, and that wet blend was added to the blender bowl.

The blended mixture was transferred to a cooker where it was cooked via direct steam injection. The mix was cooked to about 184° F. at a heating rate of about 1° F./min. The temperature was maintained at about 184° F. and blending was continued for about 2 minutes. The product was poured into 8 ounce cups, cooled and stored refrigerated until further use.

TABLE 4

Ingredients of an inventive process cheese composition.

| Ingredient | Amount (g) | Amount (%) |
|---|---|---|
| MPC-70 | 344.74 | 15.22 |
| WPC 34 | 94.80 | 2.18 |
| Dry Whey | 21.55 | 6.95 |
| Water | 679.04 | 29.94 |
| Cheese | 340.20 | 15.0 |
| AMF | 378.76 | 16.70 |
| APO | 0.46 | 0.02 |
| Annatto | 0.46 | 0.02 |
| Sorbic acid | 2.29 | 0.10 |
| MSP[1] | 7.20 | 0.32 |
| DSP[1] | 55.63 | 2.45 |
| Emulsifying salt | 34.38 | 1.52 |

TABLE 4-continued

Ingredients of an inventive process cheese composition.

| Ingredient | Amount (g) | Amount (%) |
|---|---|---|
| Condensate[2] | 204.12 | 9.0 |
| Form of Lactobionic acid[3] | 90.72 | 4.0 |

[1]No monosodium phosphate was added when the lactobionic acid was directly used. Instead, an equivalent amount of disodium phosphate was added in addition to the amount of that ingredient already specified for that ingredient in Table 4 for the formulation.
[2]The "condensate" was the water added into the cheese mass during cooking by way of condensation of steam used in the conventional direct steam injection process used in the process cheese making. The amount of condensate is dependent upon the time, temperature of cooking and the initial temperature of the mix. This amount was determined and was used in adjusting the water in the cheese composition.
[3]One of three different forms of lactobionic acid were added respectively to the three different cheese mix samples having the above composition. These three different lactobionic acid forms tested were added in solution as follows: (a) lactobionic acid dissolved in the water and used directly; (b) lactobionic acid solution, made by dissolving free acid in the water followed by neutralizing the acid solution with sodium hydroxide to a pH of about 7 before adding the lactobionic acid containing solution to the cheese mix; and (c) calcium salt of lactobionic acid, calcium lactobionate, which was dissolved in the water.

Additional process cheese samples of each of the three basic formulations described above were prepared by adjusting the lactobionic acid addition rate such that its level varied from about 1 to about 6 percent, in about 1 percent increments through that range. A level of about 4 percent lactobionic acid was found to be optimal in the process cheese products tested.

Appearance, flavor, texture and mouthfeel, and overall taste were organoleptically evaluated in a qualitative manner for each sample by a group of five evaluators using a four point scale of scoring: not acceptable, same as reference product, marginally better than reference product, and significantly better than reference product.

As the results of this evaluation, the process cheese containing the neutralized lactobionic acid was found to have an appearance similar to the control product. The texture and mouthfeel of that cheese product was also found to be on par with the control. Use of free form lactobionic acid did not contribute to any off-flavors and some evaluators commented that it enhanced cheesy/dairy notes in the product.

The process cheese products containing non-neutralized lactobionic acid and calcium lactobionate were found to have acceptable cheese flavor. The appearance, texture, and mouth feel of those samples declined at higher levels of addition (greater than about 4 percent).

EXAMPLES 7 AND 8

These examples also illustrate the inclusion of lactobionic acid in process cheeses. All ingredients of the desired process cheese formulation are mixed and pre-emulsified for 3 minutes using a Thermomix TM21 (Vorwerk) at speed setting 6 and room temperature. In Example 7, the resulting mixture is heated in a Roversi apparatus to 60° C. by indirect heating followed by direct steam hearing for 80 seconds. In Example 8, the mixture is heated in the Roversi apparatus to 50° C. by indirect heating followed by direct steam heating for 105 seconds. In both examples, the mixture is cooled to 80° C., mixed with 2 percent pre-cooked cheese ("rework"; creamed commercial product), and post creamed in a Brabender Farinograph-Resistograph, speed setting 2, at 80° C. until the viscosity plateau is reached (about 1 hour in both examples). The product is filled into containers, allowed to cool to ambient temperature, further cooled, and stored at 4° C. for at least 2 weeks.

The Brabender Farinograph used in the Examples 7 and 8 records the torque (100 Farino units=1 N m) which is related to the hot cheese viscosity.

This device is used for small-scale experimentation since it mimics the creaming tank that is used in a plant and combines it with a viscosity-recording device; such a device is, of course, not mandatory in the plant. Tests were conducted to ensure that the creaming curves obtained from both the Brabender Farinograph and the viscosity-measuring device used in the pilot plant are comparable (i.e., representative). The Farinograph is further described in detail in "The Farinograph Handbook", 3rd ed., B. L. D'Appolonia and W. H. Kunerth, eds., American Association of Cereal Chemists, St. Paul, U.S.A., 1984.

In Example 7, process cheese compositions of the following final formulations were prepared:

|  | Control 1 | Inventive Example 7 |
| --- | --- | --- |
| Dry matter | 42.0 | 40.9 |
| Fat | 17.8 | 15.0 |
| Protein | 9.9 | 9.5 |
| Lactose | 5.8 | 5.7 |
| Lactobionic acid | 0.0 | 2.0 |

All processing parameters are identical for both formulations. The incorporation of 2 percent lactobionic acid allows a solids reduction of 1.1 percent and at the same time a fat reduction of 2.8 percent.

The detailed ingredients of the samples of Example 7 are as follows:

|  | Control 1 | Inventive Example 7 |
| --- | --- | --- |
| Butter | 16.87 | 13.40 |
| Milk protein | 14.58 | 14.02 |
| Cheese | 17.50 | 17.50 |
| Melting salts | 3.15 | 3.28 |
| Water | 45.38 | 47.28 |
| Sodium chloride | 0.90 | 0.90 |
| Binding agent | 1.62 | 1.62 |
| Lactobionic acid | 0.0 | 2.0 |

Both formulations exhibit or are finally adjusted to a pH between 5.6 arid 5.9, more preferred to a pH between 5.6 and 5.8.

In Example 8, process cheese compositions of the following final formulations were prepared:

|  | Control 2 | Inventive Example 8 |
| --- | --- | --- |
| Dry matter | 40.7 | 40.1 |
| Fat | 22.2 | 18.9 |
| Protein | 12.3 | 12.3 |
| Lactose | 0.2 | 0.2 |
| Lactobionic acid | 0.0 | 3.0 |

All processing parameters are identical for both formulations. The incorporation of 3 percent of lactobionic acid allows a solids reduction of 0.6 percent and at the same time a fat reduction of 3.3 percent.

The detailed ingredients of the samples of Example 8 are as follows

|  | Control 2 | Inventive Example 8 |
| --- | --- | --- |
| Butter | 18.94 | 15.59 |
| Milk protein | 10.96 | 10.96 |
| Cheese | 11.44 | 11.44 |
| Melting salts | 3.45 | 3.45 |
| Water | 53.81 | 54.56 |
| Sodium chloride | 1.0 | 1.0 |
| Lactic acid | 0.4 | 0 |
| Lactobionic acid | 0.0 | 3.0 |

Both formulations exhibit or are finally adjusted to a pH between 5.6 and 5.9, more preferred to a pH between 5.6 and 5.8.

The creaming curves (i.e., changes in hot cheese viscosity) for Example 7 samples are shown in FIG. 8 and for Example 8 samples in FIG. 9. The creaming curves of both inventive samples closely match those of the reference (prior art) samples representing the desired hot cheese viscosity. Differences in sensory attributes (e.g., surface gloss, stickiness to the foil, creaminess, saltiness, and sourness) between the inventive and control samples could not be identified by an informal sensory evaluation.

EXAMPLE 9

This example illustrates the preparation of reduced lactose milk using lactose oxidase to convert lactose to lactobionic acid. Whole milk was pasteurized at 161° F. for 15 seconds and then cooled to 113° F. Lactose oxidase was added at a level of about 4 units/ml of milk. The reaction mixture was stirred thoroughly to disperse the enzyme. The resulting mixture was then incubated at 113° F. overnight to allow the enzymatic reaction to proceed. A control sample was exposed to the same conditions except no enzyme was added. Samples were analyzed for lactose and lactobionic acid:

|  | Control | Inventive |
| --- | --- | --- |
| Lactose | 4.45% | 1.5% |
| Lactobionic acid | 0 | 3.2% |

EXAMPLE 10

This example illustrates the biogeneration of lactobionic acid in sour cream using lactose oxidase. Formulations for a control and inventive sour cream are as follows:

|  | Amount | |
| --- | --- | --- |
| Ingredient | Control | Inventive |
| Skim milk | 52% | 52% |
| Cream | 45% | 45% |
| Water | 1% | 1% |
| Culture | 0.1% | 0.1% |
| Rennet | 0.01% | 0.01% |
| Lactose oxidase | 0 | 4 units/ml |

A mixture of skim milk, cream, and water was heated to 72° F. followed by the addition of the culture (i.e., *Lactococcus lactis* subsp. *diacetilactis* and Leuconostoc) and rennet for the control sample or the addition of culture (i.e., *Lactococcus lactis* subsp. *diacetilactis* and Leuconostoc), rennet, and lactose oxidase for the inventive sample. The mixtures were incubated at 72° F. overnight to obtain the sour cream. The amount of lactose was reduced from about 2.5 percent in the control sample to about 1.7 percent in the inventive sample using the enzyme treatment.

EXAMPLE 11

This examples illustrates the biogeneration of lactobionic acid in yogurt using lactose oxidase oxidase to generate acidity and reduce lactose levels. Milk standardized to 2% milk fat was heated to 187®F. and held at that temperature for 20 minutes. After homogenization at 150° F., the mixture was cooled to 115° F. Culture (control sample) or culture and lactose oxidase (inventive sample) were added and the mixture incubated at 113° F. for 4 hours to pH 4.6. Lactose oxidase was added at a level of about 4 units/ml of milk. The culture was a mixture of *Lactobacillus bulgaricus* and *Streptococcus thermophilus*. The control yogurt contained about 3.4 percent lactose as compared to about 0.14 percent in the enzyme treated yogurt.

EXAMPLE 12

This example illustrates the use of lactobionic acid (either directly added or generated in situ) to modify whey proteins. Whey proteins modified using lactobionic acid are more functional as process cheese ingredients compared to whey proteins modified using traditional acids. Such modified whey proteins can be used as an ingredient in cheese or other dairy products.

Sample A

WPC-35 (30.5 lbs; whey protein concentrate containing 35 percent protein) was mixed in 51.2 lb water and acidified to pH 3.78 using 3.7 lb lactobionic acid. The resulting mixture was heated to 80° C. and held for 180 minutes and spray dried to produce a powder containing 26 percent protein. The modified WPC was incorporated into a process cheese formula at 16 percent by weight. The resulting process cheese had a penetrometer firmness value of 8.6 mm compared to 11.9 mm in process cheese incorporating the same level of whey protein modified using lactic acid, and 15.4 mm for process cheese produced using an unmodified WPC-35.

Sample B

WPC-35 was reconstituted in water to a total solids concentration of 33 percent and a final lactose concentration of 15 percent. This solution was pasteurized at 70.4° C. for 15 minutes and cooled to 55° C. Lactose oxidase was added at 2 units/mL. Three liters of the reaction mixture was incubated in a 5 liter bioreactor vessel (New Brunswick) at 55° C.; pH was maintained constant at 7.0 and aeration was provided with constant sparging of filtered air and agitation at 75 rpm. The bioconversion was allowed to proceed for 48 hours resulting in the formation of the sodium salt of lactobionic acid. The pH of the resulting solution was adjusted to 3.35 with lactic acid; this was followed by heating to 176° F. for 180 minutes. The heat-treated slurry was freeze dried.

The freeze dried modified WPC was incorporated into a process cheese formula at 16 percent. The resulting process cheese had a penetrometer firmness value of 8.2 mm compared to 12.6 mm in process cheese incorporating the same level of whey protein modified using lactic acid, and 16.5 mm for process cheese produced using an unmodified WPC-35.

Sample C. WPC-35 was reconstituted in water to a total solids concentration of 33 percent and a final lactose concentration of 15 percent. This solution was pasteurized at 70.4° C. for 15 minutes and cooled to 55° C. Lactose oxidase was added at 2 units/mL. Three liters of the reaction mixture was incubated in a 5 liter bioreactor vessel (New Brunswick) at 55° C., pH was maintained constant at 7.0 using pH stat and aeration was provided with constant sparging of filtered air and agitation at 75 rpm. The bioconversion was allowed to proceed for 48 hours resulting in the formation of the sodium salt of lactobionic acid. The pH of the resulting solution was adjusted to 3.35 with lactic acid; this was followed by heating to 176° F. for 180minutes. The heat-treated slurry was cooled to 40 F and stored for use as a liquid ingredient The liquid modified WPC was incorporated into a process cheese formula at an amount providing 12% whey protein by weight. The resulting process cheese had a penetrometer firmness value of 3.9 mm compared to 14.9 mm in process cheese incorporating the same level of whey protein modified using lactic acid, and 17.7.5 mm for process cheese produced using an unmodified WPC-35.

EXAMPLE 13

This examples illustrates the use of lactobionic acid to increase the lactose derived solids in process cheese. Because of the tendency of lactose to form undesirable crystals, lactose contents are generally limited to between about 6 and about 9 percent in process cheese products depending on the specific formulation. Using lactobionic acid in addition to the lactose normally present allows higher lactose derived solids to be used in process cheese products.

Lactobionic acid 0.7 lb was combined with 2.9 lb MPC-70, 0.5 lb WPC-35, 4.7 lb dried sweet whey, and 11 lb water. This mixture was added to a melted blend of 40 lb cheddar cheese, 2 lb anhydrous milk fat, and 1.7 lb emulsifying salts. The resulting process cheese was packed into slices. The process cheese slices containing 1 percent lactobionic acid were no different from control process cheese slices containing no lactobionic acid, but had the advantage of replacing about 1 percent of the protein and fat solids with lactobionic acid.

EXAMPLE 14

This examples illustrates the use of lactobionic acid to replace milk fat in process cheese. Lactobionic acid can replace up to 25 percent of the milk fat in process cheese with slight increase in product firmness and slight melt restriction.

The following formulations were used to produce several process cheese products.

| | Amount | | |
|---|---|---|---|
| Ingredient | Control | 2% lactobionic acid | 4% lactobionic acid |
| Cheddar Cheese | 26% | 26% | 26% |
| Milk Fat | 12.6% | 10.6% | 8.6% |
| MPC-70 | 7.1% | 7.1% | 7.1% |
| WPC-34 | 13.9% | 13.9% | 13.9% |
| Dried Sweet Whey | 0.2% | 0.2% | 0.2% |
| Lactic Acid | 0.6% | 0.6% | 0.6% |

-continued

| Ingredient | Amount | | |
|---|---|---|---|
| | Control | 2% lactobionic acid | 4% lactobionic acid |
| Lactobionic Acid (neutralized with NaOH) | 0% | 2.0% | 4.0% |
| Water | 35.2% | 35.2% | 35.2% |
| Penetrometer Firmness | 26.5 mm | 21.1 mm | 23.1 mm |
| Melting Point | 50.9° C. | 64.7° C. | 66.8° C. |

Replacing milk fat with lactobionic acid increased firmness slightly and reduced melt restriction by a small amount.

Although the use of lactobionic acid has been illustrated herein in the manufacture of various types of cheeses and dairy products, it will be appreciated that the present invention also contemplates the use of lactobionic acid as a general food acidulant, an emulsifying agent, a calcium fortifier or chelater, antioxidant, and bulking agent for other types of foods in addition to dairy products.

While the invention has been particularly described with specific reference to particular process and product embodiments, it will be appreciated that various alterations, modifications and adaptions may be based on the present disclosure, and are intended to be within the spirit and scope of the present invention as defined by the following claims.

What is claimed is:

1. A process for manufacturing a cheese product containing lactobionic acid, comprising the steps of:
    preparing a liquid cheese mix comprising a dairy component, lactose, and lactobionic acid or a dietarily acceptable salt or neutralized form thereof; and
    coagulating the cheese mix to obtain the cheese product.

2. The process according to claim 1, wherein the lactobionic acid is present in an amount of about 0.1 to about 10 percent of the cheese mix.

3. The process according to claim 1, wherein the lactobionic acid is present in an amount of about 2 to about 6 percent of the cheese mix.

4. The process according to claim 1, wherein the lactobionic acid is present in an amount of about 3 to about 5 percent of the cheese mix.

5. The process according to claim 1, wherein the lactobionic acid is present in an amount effective to induce coagulation of the cheese mix.

6. The process according to claim 1, wherein the lactobionic acid is present in an amount effective to reduce the pH of the cheese mix to the isoelectric point of casein present therein.

7. The process according to claim 1, wherein the lactobionic acid is present in an amount effective to reduce the pH of the cheese mix.

8. The process according to claim 1, wherein the lactobionic acid is an alkali salt or an alkaline earth metal salt of lactobionic acid.

9. The process according to claim 1, wherein the lactobionic acid is a sodium, potassium, or calcium salt of lactobionic acid.

10. The process according to claim 1, wherein the lactobionic acid is a free acid.

11. The process according to claim 1, wherein the lactobionic acid is added to the cheese mix as a solution of lactobionate salt dissolved in water and neutralized to a pH of about 7 by addition of an alkaline substance.

12. The process according to claim 1, wherein the cheese mix further comprises an enzymatic coagulant.

13. The process according to claim 1, further comprising the steps of forming curd and whey from the coagulated mix, and separating the curd from the whey to obtain the cheese product.

14. The process according to claim 1, wherein the cheese mix further comprises a starter culture.

15. The process according to claim 1, wherein the cheese mix further including further comprises a lactic acid bacteria in amount effective for culturing the cheese mix.

16. The process according to claim 1, wherein the dairy component is selected from the group consisting of fluid milk, concentrated milk, UF permeate, whey protein concentrate, cream, sweet cream, milk solids, dairy by-products streams, and mixtures thereof.

17. The process according to claim 16, wherein the cheese product is cream cheese.

18. The process according to claim 16, wherein the cheese product is cheddar cheese.

19. A process for manufacturing a process cheese product containing lactobionic acid, said comprising the steps of:
    preparing a cheese mix comprising lactose, comminuted solid cheese, and lactobionic acid or a dietarily acceptable salt or neutralized form thereof;
    heating the cheese mix at a temperature and for a time to yield a melted cheese blend;
    heating the melted cheese blend at a temperature between about 170° F. and about 200° F. for between about one and ten minutes to provide the process cheese product; and packaging the process cheese product.

20. A cheese product comprising cheese and lactobionic acid or a dietarily acceptable salt or neutralized form thereof, wherein the lactobionic acid or dietarily acceptable salt or neutralized form thereof is present in an amount of about 0.1 to about 10 percent of the cheese product.

21. The cheese product of claim 20, wherein the cheese product is a process cheese product.

22. A process for manufacturing a dairy product containing lactobionic acid, comprising the steps of:
    preparing a liquid mix comprising a dairy component, lactose, and lactobionic acid or a dietarily acceptable salt or neutralized form thereof; and
    treating the liquid mix to obtain the dairy product.

23. The process of claim 22, wherein the dairy component is selected from the group consisting of fluid milk, concentrated milk, UF permeate, whey protein concentrate, cream, sweet cream, milk solids, dairy by-products streams, and mixtures thereof.

24. The process according to claim 23, wherein the lactobionic acid is added to the cheese mix as a solution of lactobionate salt dissolved in water and neutralized to a pH of about 7 by addition of an alkaline substance.

25. The process according to claim 23, wherein the dairy product comprises cheese.

26. The process according to claim 23, wherein the dairy product comprises yogurt.

27. The process according to claim 23, wherein the dairy product comprises sour cream.

28. The process according to claim 23, wherein the dairy product comprises cottage cheese.

29. The process according to claim 23, wherein the dairy product comprises buttermilk.

30. The process according to claim 23, wherein the dairy product comprises milk.

31. The process according to claim 23, wherein the dairy product comprises a whey-containing product.

32. A process cheese comprising about 0.1 to about 10 percent of lactobionic acid and/or a salt thereof, wherein the process cheese has a dry matter content of about 25 to about 60 percent and a fat content of about 5 to about 40 percent.

33. The process cheese of claim 32, wherein the amount of lactobionic acid and/or a salt thereof is about 0.5 to about 7 percent.

34. The process cheese of claim 33, wherein the amount of lactobionic acid and/or a salt thereof is about 1 to about 5 percent.

35. A process for preparing process cheese, said process comprising the steps of:
(a) mixing process cheese formulation ingredients with lactobionic acid and/or a salt thereof to form a mixture;
(b) heat treating the mixture;
(c) cooling the heat-treated mixture; and
(d) post-creaming the cooled mixture to a desired viscosity level.

36. The process according to claim 35, wherein the mixture in step (b) is heated at a temperature of about 105 to about 150° C. for about 2 seconds to about 20 minutes and wherein the heat-treated mixture in step (c) is cooled to about 70 to about 95° C.

37. The process according to claim 36, wherein the desired viscosity level achieved in step (d) is a time-independent viscosity level.

* * * * *

UNITED STATES PATENT AND TRADEMARK OFFICE
CERTIFICATE OF CORRECTION

PATENT NO. : 6,916,496 B2
APPLICATION NO. : 10/702718
DATED : July 12, 2005
INVENTOR(S) : Koka et al.

Page 1 of 1

It is certified that error appears in the above-identified patent and that said Letters Patent is hereby corrected as shown below:

On cover page, insert
        (30) Foreign Application Priority Data
May 7, 2001  (EPO)………………………...01110166.4

In claim 15, column 24, line 10, delete "including further".

In claim 15, column 24, line 11, after "in", insert -- an --.

In claim 19, column 24, line 22, delete "said".

Signed and Sealed this

Eighteenth Day of July, 2006

JON W. DUDAS
*Director of the United States Patent and Trademark Office*